United States Patent
Shimazu

(10) Patent No.: US 9,102,587 B2
(45) Date of Patent: Aug. 11, 2015

(54) METHOD FOR PRODUCING 2-(ISOPROPYLAMINO)ETHANOL

(71) Applicant: KOEI CHEMICAL COMPANY, LIMITED, Osaka (JP)

(72) Inventor: Hidetaka Shimazu, Chiba (JP)

(73) Assignee: KOEI CHEMICAL COMPANY, LIMITED, Osaka (JP)

( * ) Notice: Subject to any disclaimer, the term of this patent is extended or adjusted under 35 U.S.C. 154(b) by 0 days.

(21) Appl. No.: 14/407,513

(22) PCT Filed: Jul. 12, 2013

(86) PCT No.: PCT/JP2013/004305
§ 371 (c)(1),
(2) Date: Dec. 12, 2014

(87) PCT Pub. No.: WO2014/013706
PCT Pub. Date: Jan. 23, 2014

(65) Prior Publication Data
US 2015/0183718 A1 Jul. 2, 2015

(30) Foreign Application Priority Data
Jul. 20, 2012 (JP) ................................. 2012-161125

(51) Int. Cl.
*C07C 213/08* (2006.01)
*C07C 213/02* (2006.01)

(52) U.S. Cl.
CPC ............ *C07C 213/08* (2013.01); *C07C 213/02* (2013.01)

(58) Field of Classification Search
CPC ...................................................... C07C 213/08
See application file for complete search history.

(56) References Cited

U.S. PATENT DOCUMENTS

| 7,009,081 B2 * | 3/2006 | Mitchell et al. | ................ 564/474 |
| 2011/0137030 A1 | 6/2011 | Kubanek et al. | |
| 2012/0116126 A1 * | 5/2012 | Ruppin et al. | ................ 564/473 |

FOREIGN PATENT DOCUMENTS

| JP | 2009-173553 | 8/2009 |
| WO | 2011/067199 | 6/2011 |

OTHER PUBLICATIONS

Hancock, E. et al., 2-Isopropylaminoethanol, Organic Syntheses, 1946, vol. 26, p. 38.
International Search Report for PCT/JP2013/004305, dated Oct. 8, 2013.

* cited by examiner

*Primary Examiner* — Brian J Davis
(74) *Attorney, Agent, or Firm* — Roylance, Abrams, Berdo & Goodman, L.L.P.

(57) ABSTRACT

The present invention relates to a method of producing 2-(isopropylamino)ethanol, including subjecting acetone, 2-aminoethanol, and hydrogen to a vapor-phase catalytic reaction in the presence of a noble metal-containing catalyst. According to the present invention, 2-(isopropylamino)ethanol can be industrially obtained in a large amount and with high efficiency through the vapor-phase catalytic reaction of acetone, 2-aminoethanol, and hydrogen. 2-(Isopropylamino)ethanol is a compound useful as a raw material for a drug, an agricultural chemical, or the like.

15 Claims, No Drawings

METHOD FOR PRODUCING 2-(ISOPROPYLAMINO)ETHANOL

TECHNICAL FIELD

The present invention relates to a method of producing 2-(isopropylamino)ethanol, which is a compound useful as a raw material for a drug, an agricultural chemical, or the like.

BACKGROUND ART

Known methods of producing 2-(isopropylamino) ethanol are as follows:
(1) a method involving allowing acetone to react with 2-aminoethanol and hydrogen at from 1 to 2 atm in the presence of a platinum oxide catalyst in ethanol to produce 2-(isopropylamino) ethanol (Non Patent Literature 1); and
(2) a method involving allowing acetone to react with a mixture of 2-aminoethanol and hydrogen at 4.5 MPa in the presence of a palladium-carbon catalyst in methanol to produce 2-(isopropylamino)ethanol (Patent Literature 1).

PRIOR ART DOCUMENTS

Patent Literature

[PTL 1] JP 2009-173553 A

Non Patent Literature

[NPL 1] Organic Syntheses, 1946, Vol. 26, p. 38

SUMMARY OF INVENTION

Technical Problem

As described above, there has been reported a method involving allowing acetone to react with 2-aminoethanol and hydrogen under increased pressure in the presence of a platinum oxide catalyst or palladium-carbon catalyst in an alcohol solvent to produce 2-(isopropylamino)ethanol. However, there has yet to be a report of a method involving subjecting acetone, 2-aminoethanol, and hydrogen to a vapor-phase catalytic reaction in the presence of a noble metal-containing catalyst to produce 2-(isopropylamino)ethanol. Accordingly, it has been desired to develop a method of industrially producing 2-(isopropylamino)ethanol with high efficiency through a vapor-phase catalytic reaction.

Solution to Problem

The inventor of the present invention has made intensive studies in view of such circumstances. As a result, the inventor has found that 2-(isopropylamino)ethanol is obtained with high efficiency by subjecting acetone, 2-aminoethanol, and hydrogen to a vapor-phase catalytic reaction in the presence of a noble metal-containing catalyst. Thus, the inventor has completed the present invention.

That is, the present invention relates to a method of producing 2-(isopropylamino)ethanol, including subjecting acetone, 2-aminoethanol, and hydrogen to a vapor-phase catalytic reaction in presence of a noble metal-containing catalyst.

Advantageous Effects of Invention

According to one embodiment of the present invention, 2-(isopropylamino)ethanol can be obtained in a large amount and with high efficiency through the vapor-phase catalytic reaction. Therefore, the method of the present invention is industrially useful as a method of producing 2-(isopropylamino)ethanol.

DESCRIPTION OF EMBODIMENTS

The present invention is described in detail below.
According to one embodiment of the present invention, there is provided a method of producing 2-(isopropylamino) ethanol, including subjecting acetone, 2-aminoethanol, and hydrogen to a vapor-phase catalytic reaction in the presence of a noble metal-containing catalyst.

A reaction temperature in the present invention is generally from 80 to 250° C., preferably from 100 to 150° C., more preferably from 125 to 135° C. The reaction is performed under normal pressure or under increased pressure. The mode of the reaction is not particularly limited. The reaction is performed in a fixed bed, a fluidized bed, or a moving bed, and any one of the batch and continuous modes may be adopted.

The amount of acetone to be used is generally 0.5 mol or more, preferably from 2 to 6 mol with respect to 1 mol of 2-aminoethanol.

Purchased 2-aminoethanol may be used as it is for the reaction, or an aqueous solution or organic solvent solution of 2-aminoethanol may be used. When the aqueous solution or organic solvent solution is used, its concentration is not particularly limited and may be appropriately determined depending on the scale of the reaction.

As the noble metal-containing catalyst, a known one may be used, and the noble metal-containing catalyst is preferably a catalyst containing one or more kinds of palladium, platinum, and ruthenium, more preferably a catalyst containing one or more kinds of palladium and platinum.

The noble metal-containing catalyst may contain an element other than those described above as a second component in addition to the noble metal. Examples of the element include rhenium, tellurium, bismuth, antimony, gallium, indium, sulfur, phosphorus, selenium, and germanium.

The noble metal-containing catalyst may be used by being supported on a support. The support may be any support that is generally used as a support for a catalyst. Specific examples of the support include alumina, silica, silica-alumina, silicon carbide, zirconium oxide, magnesium oxide, cerium oxide, titanium oxide, and various zeolites. Of those, alumina or silica is preferred, and alumina is particularly preferred. The support has a surface area of generally from 40 to 500 $m^2/g$, preferably from 100 to 350 $m^2/g$. The amount of the noble metal to be supported on the support is not particularly limited, but is generally from 0.5 to 5 wt %, preferably from 0.5 to 2 wt %, more preferably from 0.5 to 1 wt % with respect to the support.

Specific examples of the noble metal-containing catalyst include a platinum-alumina catalyst, a platinum-carbon catalyst, a platinum-black catalyst, a palladium-alumina catalyst, a palladium-carbon catalyst, a palladium-black catalyst, a ruthenium-alumina catalyst, a ruthenium-carbon catalyst, and a ruthenium-black catalyst. Preferred specific examples of the catalyst include a palladium-alumina catalyst and a platinum-alumina catalyst.

A method of preparing the noble metal-containing catalyst is not particularly limited. Examples of the method of preparing the noble metal-containing catalyst include a kneading method, an impregnation method, and a coprecipitation method. The shape of the noble metal-containing catalyst is, for example, a shape prepared by extrusion or by tableting into an arbitrary shape. In addition, the shaped noble metal-containing catalyst may be used after being fired under an atmosphere of an arbitrary gas such as nitrogen at from 150 to 500° C.

The noble metal-containing catalyst is preferably used for the reaction after being subjected to reduction treatment. A reducing agent to be used for the reduction treatment is not particularly limited, but is preferably hydrogen. A method of reducing the noble metal-containing catalyst is not particularly limited, but is preferably heat treatment under a hydrogen flow. The flow rate of hydrogen in the reduction treatment is generally SV=100 to 500/hr, preferably SV=200 to 400/hr. The hydrogen may be diluted with an inert gas such as nitrogen or argon. A temperature at which the reduction with hydrogen is performed is generally from 50 to 400° C., preferably from 100 to 150° C., more preferably from 125 to 135° C.

At the time of the reaction, it is preferred to flow hydrogen at the same time as 2-aminoethanol and acetone are flowed, because in this case, the yield of 2-(isopropylamino) ethanol is improved. The amount of hydrogen to be used in that case is generally from 1 to 20 mol, preferably from 5 to 12 mol with respect to 1 mol of 2-aminoethanol.

2-Aminoethanol and acetone are generally mixed before being introduced into a reactor. The space velocity of the mixture in the reactor is generally from 0.01 to 2 (g/cc-catalyst·h), preferably from 0.1 to 1 (g/cc-catalyst·h) in terms of liquid hourly space velocity (LHSV).

The reaction is performed in the presence or absence of a diluent. Any diluent may be used without any particular limitation as long as the diluent is inert to the reaction. Specific examples of the diluent that may be used include: an inert gas such as nitrogen or argon; an aliphatic hydrocarbon such as hexane, heptane, octane, nonane, decane, or undecane; and a halogenated aliphatic hydrocarbon such as dichloromethane or 1,2-dichloroethane. One kind of those diluents may be used alone, or two or more kinds thereof may be used as a mixture.

The 2-(isopropylamino) ethanol generated through the reaction may be collected by general means such as cooling of a reacted gas to be obtained or absorption of the reacted gas into water or a solvent after the completion of the reaction. The collected 2-(isopropylamino)ethanol may be isolated/purified by general purification means such as distillation.

EXAMPLES

Next, the present invention is specifically described by way of Examples. However, the present invention is by no means limited to Examples below. It should be noted that analysis by gas chromatography in Examples was performed under the following conditions.

Conditions for Gas Chromatography Analysis
Gas chromatograph: GC-2010 manufactured by Shimadzu Corporation
Column: manufactured by J&W Scientific Incorporated, HP-1, 50 m,
inner diameter: 0.32 mm, film thickness: 1.05 μm
Temperature: 50° C.→(10° C./min)→250° C.

In addition, the conversion rate and yield were calculated according to the following definitions.

Conversion rate (o)=reacted 2-aminoethanol (mol)/2-aminoethanol supplied for reaction (mol)×100

Yield (%)=produced 2-(isopropylamino)ethanol (mol)/2-aminoethanol supplied for reaction (mol)×100

Example 1

A reaction tube having an inner diameter of 20 mm was filled with 520 ml of 1 wt % palladium-alumina pellets (manufactured by N.E. CHEMCAT Corporation, cylindrical shape measuring 3.2 mm in diameter by 3 mm in height) as a catalyst, and was filled with a 100-cm length each of Carborundum on and below the catalyst. The reaction tube was heated to a temperature of from 128 to 132° C., and a mixture of hydrogen at 1 l/min and nitrogen at 1 l/min was flowed from an upper portion for 1 hour to perform pretreatment of the catalyst. After the completion of the pretreatment of the catalyst, a mixture of 2-aminoethanol, acetone, and hydrogen (mixing molar ratio: 2-aminoethanol:acetone:hydrogen=1:4:9) was flowed through the reaction tube at LHSV=0.5 g/cc-catalyst·hr (mixture of 2-aminoethanol and acetone) from an upper portion to perform a reaction at from 128 to 132° C. A reacted gas discharged from the reaction tube was absorbed into cooled water, and then the absorption liquid was analyzed by gas chromatography. Between 95 to 99 hours after the initiation of the reaction, the average conversion rate of 2-aminoethanol was 100% and the average yield of 2-(isopropylamino)ethanol (based on 2-aminoethanol) was 96.0%.

Example 2

A reaction was performed in the same manner as in Example 1 except that: 0.5 wt % platinum-alumina pellets (manufactured by N.E. CHEMCAT Corporation, cylindrical shape measuring 3.2 mm in diameter by 3 mm in height) were used as the catalyst; the molar ratio was set to 2-aminoethanol:acetone:hydrogen=1:3:9; and the LHSV was set to 0.58 g/cc-catalyst·hr (mixture of 2-aminoethanol and acetone). Between 77 to 93 hours after the initiation of the reaction, the average conversion rate of 2-aminoethanol was 100% and the average yield of 2-(isopropylamino)ethanol (based on 2-aminoethanol) was 95.7%.

Comparative Example 1

A reaction was performed in the same manner as in Example 1 except that copper oxide/zinc oxide Actisorb (trademark) 301 (manufactured by Süd-Chemie, extruded product having a diameter of 1.5 mm) was used as the catalyst. As a result, the yield of 2-(isopropylamino)ethanol was 5% or less.

Comparative Example 2

A reaction was performed in the same manner as in Example 1 except that γ-alumina (manufactured by Sumitomo Chemical Company, Limited, spherical shape having a diameter of from 2 to 4 mm) was used as the catalyst. As a result, the yield of 2-(isopropylamino)ethanol was 5% or less.

Comparative Example 3

A reaction was performed in the same manner as in Example 1 except that stabilized nickel (manufactured by JGC Catalysts and Chemicals Ltd., cylindrical shape measuring 2.8 mm in diameter by 2.8 mm in height) was used as the catalyst. As a result, the yield of 2-(isopropylamino)ethanol was 5% or less.

INDUSTRIAL APPLICABILITY

According to one embodiment of the present invention, 2-(isopropylamino)ethanol can be obtained in a large amount and with high efficiency by subjecting acetone, 2-aminoethanol, and hydrogen to a vapor-phase catalytic reaction in the presence of a noble metal-containing catalyst.

The invention claimed is:

1. A method of producing 2-(isopropylamino)ethanol, comprising subjecting acetone, 2-aminoethanol, and hydrogen to a vapor-phase catalytic reaction in the presence of a noble metal-containing catalyst.

2. The method of producing 2-(isopropylamino)ethanol according to claim 1, wherein the noble metal-containing catalyst comprises a catalyst containing at least one kind of noble metal selected from the group consisting of palladium, platinum, and ruthenium.

3. The method of producing 2-(isopropylamino)ethanol according to claim 1, wherein the noble metal-containing catalyst comprises a noble metal-containing catalyst subjected to reduction treatment before use.

4. The method of producing 2-(isopropylamino)ethanol according to claim 1, wherein the noble metal-containing catalyst comprises a noble metal-containing catalyst subjected to hydrogen reduction treatment before use.

5. The method of producing 2-(isopropylamino)ethanol according to claim 1, wherein the noble metal-containing catalyst comprises a noble metal-containing catalyst subjected to hydrogen reduction treatment at from 100 to 150° C. before use.

6. The method of producing 2-(isopropylamino)ethanol according to claim 1, wherein the noble metal-containing catalyst comprises a noble metal-containing catalyst supported on a support.

7. The method of producing 2-(isopropylamino)ethanol according to claim 6, wherein the support comprises at least one kind of support selected from the group consisting of alumina, silica, and silica-alumina.

8. The method of producing 2-(isopropylamino)ethanol according to claim 1, wherein the vapor-phase catalytic reaction is performed at from 100 to 150° C.

9. A method of producing 2-(isopropylamino)ethanol, comprising absorbing, into water, a reacted gas obtained by subjecting acetone, 2-aminoethanol, and hydrogen to a vapor-phase catalytic reaction in the presence of a noble metal-containing catalyst.

10. The method of producing 2-(isopropylamino)ethanol according to claim 2, wherein the vapor-phase catalytic reaction is performed at from 100 to 150° C.

11. The method of producing 2-(isopropylamino)ethanol according to claim 3, wherein the vapor-phase catalytic reaction is performed at from 100 to 150° C.

12. The method of producing 2-(isopropylamino)ethanol according to claim 4, wherein the vapor-phase catalytic reaction is performed at from 100 to 150° C.

13. The method of producing 2-(isopropylamino)ethanol according to claim 5, wherein the vapor-phase catalytic reaction is performed at from 100 to 150° C.

14. The method of producing 2-(isopropylamino)ethanol according to claim 6, wherein the vapor-phase catalytic reaction is performed at from 100 to 150° C.

15. The method of producing 2-(isopropylamino)ethanol according to claim 7, wherein the vapor-phase catalytic reaction is performed at from 100 to 150° C.

* * * * *